United States Patent [19]

Fraiser et al.

[11] Patent Number: 5,702,926
[45] Date of Patent: Dec. 30, 1997

[54] NICKING OF DNA USING BORONATED NUCLEOTIDES

[75] Inventors: Melinda S. Fraiser, Durham; George Terrance Walker, Chapel Hill, both of N.C.

[73] Assignee: Becton, Dickinson and Company, Franklin Lakes, N.J.

[21] Appl. No.: 701,270

[22] Filed: Aug. 22, 1996

[51] Int. Cl.$^6$ .................... C12P 19/34; C12N 11/00; C07H 21/00

[52] U.S. Cl. .................. 435/91.2; 435/174; 435/91.1; 536/25.3

[58] Field of Search ..................... 435/91.2, 174, 435/91.1; 536/22.1, 25.3

[56] References Cited

U.S. PATENT DOCUMENTS

| 5,270,184 | 12/1993 | Walker et al. | 435/91.2 |
| 5,434,143 | 7/1995 | Spielvogel | 514/64 |
| 5,455,166 | 10/1995 | Walker | 435/91.2 |

*Primary Examiner*—Kenneth R. Horlick
*Assistant Examiner*—Joyce Tung
*Attorney, Agent, or Firm*—Donna R. Fugit

[57] ABSTRACT

α-Boronated deoxynucleoside triphosphates, when incorporated into a double-stranded restriction endonuclease recognition/cleavage site for a restriction endonuclease, induce nicking by the restriction endonuclease. α-Boronated deoxynucleoside triphosphates (dNTPαBH$_3$) are therefore useful as nucleotide analogs in SDA to produce the nickable hemimodified restriction endonuclease recognition/cleavage site required to sustain the amplification reaction.

10 Claims, No Drawings

[5,702,926]

NICKING OF DNA USING BORONATED NUCLEOTIDES

FIELD OF THE INVENTION

The present invention relates to methods for inducing nicking by restriction endonucleases, methods for amplification of target nucleic acid sequences, and in particular to amplification by Strand Displacement Amplification (SDA).

BACKGROUND OF THE INVENTION

In vitro nucleic acid amplification techniques are powerful tools for detection and analysis of small amounts of nucleic acids, and the high degree of sensitivity of these methods has generated interest in developing them for diagnosis of infectious and genetic diseases, isolation of genes for analysis, and detection of specific nucleic acids as in forensic medicine. Nucleic acid amplification methods include, for example, the Polymerase Chain Reaction (PCR), the Ligase Chain Reaction (LCR), Self Sustained Sequence Replication (3SR), Nucleic Acid Sequence Based Amplification (NASBA), Transcription Mediated Replication (TMR) and Strand Displacement Amplification (SDA). Strand Displacement Amplification is an isothermal amplification reaction which is capable of producing greater than a billion-fold amplification of a target sequence in less than 30 min. at constant temperature (G. T. Walker, et al. 1992. *Proc. Natl. Acad. Sci. USA* 89, 392–396; G. T. Walker, et at. 1992. *Nuc. Acids. Res.* 20, 1691–1696; U.S. Pat. No. 5,455, 166; U.S. Pat. No. 5,270,184; EP 0 684 315).

The SDA reaction may be conducted at a constant temperature between about 37° C. and 42° C. or at constant higher temperatures to improve amplification efficiency and specificity (thermophilic SDA or tSDA as described in published European Patent Application No. 0 684 315). In either format, SDA employs 1) a restriction endonuclease which nicks a hemimodified restriction endonuclease recognition/cleavage site and 2) a polymerase which extends from the nick and displaces a copy of the target sequence while polymerizing a new strand using the target sequence as a template. Repeated cycles of nicking and displacing produce additional copies of the target sequence.

The SDA reaction is described in U.S. Pat. No. 5,455,166, U.S. Pat. No. 5,270,184 and EP 0 684 315. The steps of the SDA reaction are the same regardless of the temperature and enzymes employed, and it requires several specific enzymatic activities in order to successfully amplify a target sequence. The SDA polymerase must 1) lack 5'-3' exonuclease activity, either naturally or by inactivation, 2) incorporate the derivatized deoxynucleoside triphosphates (dNTPs) required by SDA (nucleotide analogs such as αthio-dNTPs), 3) displace a downsteam single strand from a double stranded molecule starting at a single stranded nick, and preferably 4) incorporate dUTP to allow amplicon decontamination. The SDA restriction endonuclease must 1) nick (i.e., cleave a single strand of) its double stranded recognition/cleavage site when the recognition/cleavage site is hemimodified, 2) dissociate from its recognition/cleavage site to allow the polymerase to bind and amplify the target, and preferably 3) be unaffected by dUTP incorporated into its recognition/cleavage site. Incorporation of the dNTP analog into the restriction endonuclease recognition site induces nicking by the restriction endonuclease. Thiolated dNTPs are the most commonly used nucleotide analog in SDA, however, incorporation of methyl-substituted dNTPs also induces nicking. Examples of polymerases and restriction endonucleases having the appropriate biological activities for SDA are described in the patent publications cited above. Terms relating to amplification by SDA are defined in EP 0 684 315.

SUMMARY OF THE INVENTION

It has now been found that alpha-boronated deoxynucleoside triphosphates, when incorporated into a double-stranded restriction endonuclease recognition/cleavage site for a restriction endonuclease to produce a hemimodified recognition/cleavage site, induce nicking (cleavage of one of the two strands) by the restriction endonuclease. Alpha-boronated deoxynucleoside triphosphates (dNTPαBH$_3$) are therefore useful in SDA to produce the nickable hemimodified restriction endonuclease recognition/cleavage site required to sustain the amplification reaction.

DETAILED DESCRIPTION OF THE INVENTION

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. Strand displacing activity makes the target available for synthesis of additional copies and generates the single stranded extension product to which a second amplification primer hybridizes in exponential amplification reactions. As incorporation of dNTP analogs induces nicking by the restriction endonuclease, the polymerase must be capable of incorporating the selected deoxynucleotide analog as well as displacing a strand containing it.

Several polymerases have been identified as having the required characteristics for use in SDA when thiolated or methylated dNTPs are used: exo⁻ Klenow, T5 DNA polymerase, and Phi29 DNA polymerase, exo⁻ Vent (New England Biolabs), exo⁻ Deep Vent (New England Biolabs), Bst (BioRad), exo⁻ Pfu (Stratagene), Bca (Panvera), and Sequencing Grade Taq (Promega). The polymerases Tth (Boehringer), Tfl (Epicentre), REPLINASE (DuPont) and REPLITHERM (Epicentre) strand displace from a nick, but also have 5'-3' exonuclease activity. These polymerases are useful in the methods of the invention after removal of the exonuclease activity, e.g., by genetic engineering. Routine screening assays as described below may be used to determine whether or not a polymerase has the required characteristics when a dNTP with a new substitution is desired.

Nicking activity is essential to SDA, as it is nicking which perpetuates the reaction and allows subsequent rounds of target amplification to initiate. That is, restriction endonucleases suitable for SDA also must cleave only one of the two strands of a double stranded hemimodified recognition/ cleavage site for the restriction endonuclease ("nicking"). The restriction endonuclease must then dissociate from the recognition/cleavage site to allow the polymerase to bind at the nick and initiate extension. Because restriction enzymes generally produce double-stranded breaks, cleavage of one of the two strands in the duplex of the cleavage site must be selectively inhibited. In SDA, this is accomplished by introducing at least one substituted nucleotide (a nucleotide analog) into the restriction endonuclease recognition site during polymerizationto produce a hemimodified site. Routine screening assays as described below may be used to determine whether or not nicking is induced when a new nucleotide analog is incorporated into a hemimodified restriction endonuclease recognition site.

Deoxynucleotide phosphorothioates and methylated nucleotides have been used to induce nicking in SDA.

Examples of restriction endonuclease recognition sites which are useful in SDA and the deoxynucleotide analogs which induce nicking of those sites are described in U.S. Pat. No. 5,455,166 and EP 0 684 315. The present invention provides a new group of dNTP analogs (alpha-boronated dNTPs) which are incorporated by polymerases during SDA and which induce nicking by the restriction endonuclease to sustain the amplification reaction. The corresponding alpha-boronated dNTP may be substituted for any of the dNTP analogs set forth in these publications, in SDA reactions employing the appropriate restriction endonuclease and recognition site as described.

Boronated deoxynucleoside triphosphate compounds (available from Boron Biologicals) are screened in three assays to evaluate and predict their utility in SDA. The first is a polymerase activity assay used to determine whether or not a polymerase is capable of incorporating the boronated dNTPs. In one polymerase activity assay, activated thymus DNA was used as a substrate for varying dilutions of polymerase. The selected polymerase was diluted in an enzyme diluent comprising 25 mM potassium phosphate, 5 mM ammonium sulfate, 10 mM 2-mercaptoethanol and 1 mg/ml BSA. Ten µl of the dilution was added to a buffer for the assay (25 mM potassium phosphate, 0.15 mM each dNTP and dNTP analog, 4 mM magnesium chloride, 4.5 µg activated calf thymus DNA, and 0.3 µl of 3000 mCi/mmol $^{32}$P-labeled dNTP). After equilibration, the reaction was incubated at the reaction temperature for 15 min. At time intervals, 15 µl of the reaction was removed and added to 45 µl of 25 mM EDTA to stop the reaction. Forty µl of the terminated reaction was spotted onto a DE-81 filter disk and washed at least four times in 10 ml 0.3M ammonium formate pH 8.0 for 5 min. each wash. After the final wash, the filters were rinsed in methanol, air dried on absorbent paper, placed in scintillation vials with scintillation fluid and counted.

For example, Bca polymerase (Takara or PanVera) incorporation of dCTPαBH$_3$ at 60° C. was tested in the polymerase activity assay with reference to dCTP and dCTPαS as controls. The dCTP control was assayed at 1:30,000 and 1:40,000 dilutions. The dCTPαS control was assayed at 1:20,000 and 1:30,000 dilutions and the boronated dCTP was assayed at 1:20,000, 1:30,000 and 1:40,000 dilutions. Results were counted at three time points (5, 10 and 15 min.) and compared to background readings for blank filters. Bca polymerase incorporating unmodified dCTP gave an activity of 152 units/µl. Full substitution with dCTPαS caused a drop in polymerase activity to 39 units/µl. Reduced activity of polymerases in the presence of thiolated dNTPs has been previously observed, but does not appear to interfere significantly with SDA efficiency. Full substitution with dCTPαBH$_3$ resulted in a reduction in polymerase activity similar to that of dCTPαS (40–50 units/µl). Based on these results, it would be expected that SDA polymerases would be capable of incorporating other boronated dNTPs as well (e.g., dATPαBH$_3$, TTPαBH$_3$ or dGTPαBH$_3$), as the polymerase activity assay demonstrates that alpha-boronation of dNTPs does not prevent the polymerization reaction.

A polymerase extension assay is used to evaluate the ability of polymerases to strand-displace in the presence of boronated deoxynucleoside triphosphates. In one polymerase extension assay, the nick which is essential to sustain the SDA reaction is staged by annealing an upstream, labeled primer adjacent to a downstream, unlabeled primer on an AluI digested M13 plasmid. The plasmid is digested to provide a defined stopping point for the polymerase which would produce band of defined size on a gel. In this example, the assay was conducted in 25 mM K$_2$PO$_4$, pH 7.5, 0.1 µg/µl BSA, 1 mM each dNTP, 250 ng digested target plasmid, polymerase and 40 nM upstream displacing primer radioactively end-labeled with polynucleotide kinase. Thiolated or boronated dCTP was present in varying amounts and 40 nM of the downstream primer was either present or absent in each reaction. The mixture was denatured at 100° C. for 3 min. and cooled for 2 min. at the reaction temperature appropriate for the polymerase. The polymerase being tested was then added and the extension reaction was allowed to continue for 10 min. Extension was stopped by addition of 25 mM EDTA/98% formamide. The samples were then electrophoresed over denaturing gels and analyzed by autoradiography. If the polymerase displaced the downstream primer and fully extended the upstream labeled primer, a band of defined size would be observed. The amount of the product band indicated the efficiency of primer extension by the polymerase.

Bca polymerase (tested at 60° C.) performed equally well in the extension assay with either boronated dCTP or dCTPαS. In the absence of the downstream primer, equal amounts of extension product were observed in the presence of the various nucleotide analogs, indicating equally efficient incorporation. When the downstream primer was present, all reactions produced less of the fully extended product with the appearance of shorter abortive products. Although more of the abortive products were observed in the dCTPαBH$_3$ reaction than in the dCTPαS reaction, boronated dCTPs were considered comparable to thiolated dCTP in the assay. Based on these results, it would be expected that SDA polymerases would extend and displace in the presence of other boronated dNTPs (e.g., dATPαBH$_3$, TTPαBH$_3$ or dGTPαBH$_3$), as the assay demonstrates that boron derivitization does not prevent these polymerase activities.

All nucleotide analogs may not induce nicking by all restriction endonucleases. An assay for evaluating the nicking characteristics of restriction endonucleases in the presence of a selected nucleotide analog was therefore developed based on the ability of a modified deoxynucleoside triphosphate incorporated into the double-stranded restriction endonuclease recognition/cleavage site to protect one of the two strands from cleavage by the endonuclease. This is referred to as the analog-induced nicking assay or the strand protection assay. In the strand protection assay, a single stranded template containing the selected restriction endonuclease recognition site and primer complementary to the 3' end of the template are synthesized. The template and the primer are then labeled, preferably with a radiolabel. The primer and template are hybridized and the selected modified dNTPs (nucleotide analogs) are incorporated into one strand by extension of the primer, producing a fully double stranded molecule containing a hemimodified restriction endonuclease recognition/cleavage site. This product is treated with the restriction endonuclease under conventional conditions for cleavage. Electrophoretic analysis of the reaction products under denaturing conditions is used to determine, by the size of the fragments generated, whether or not the recognition/cleavage site was nicked, cleaved through both strands or uncut. The size of the fragments on electrophoresis may also be used to determine which of the two strands of the recognition/cleavage site (i.e., modified or unmodified) was protected from cleavage.

For example, a 45-mer template containing a BsoBI site (CTCGGG) and a 21-mer complementary to the 3' portion of the template were synthesized. Either the template or the primer was radioactively end-labeled using polynucleotide kinase. The 21-mer was hybridized to the template and the hemimodified BsoBI restriction site was constructed by extending the 21-mer on the template in the presence of α-boronated dCTP (dCTPαBH₃) as follows. Reactions containing 35 mM K₂PO₄, pH 7.5; 0.1 μg/μl BSA; 1 mM each TTP, dATP, dGTP and dCTP; dCTPαBH₃ or α-thio-dCTP (dCTPαS); 50 nM template (labeled or unlabeled) and 50 nM primer (labeled or unlabeled) were assembled. The DNA was denatured at 100° C. for 2 min. and the reactions were cooled to 37° C. for 2 min. Eight units of exo⁻ Klenow polymerase were added and the extension reaction was allowed to proceed at 37° C. for 30 min. in the presence of the selected dCTP reagent. The polymerase was heat-inactivated at 60° C. for 10 min. and 10 μl of the reaction was removed for use as the control. Twenty units of BsoBI in 35 mM K₂PO₄, 0.1 μg/μl BSA was added and the cleavage reaction was incubated at 60° C. for 15 min. The cleavage reaction was stopped by addition of 25 mM EDTA/98% formamide. The reactions were then electrophoresed over 8% denaturing gels and the results were visualized by autoradiography. The modified strand of the hemi-modified restriction site for BsoBI was completely protected by incorporation of either dCTPαBH₃ or dCTPαS, with efficient cleavage of the unmodified strand (nicking). Observation of nicking activity in the strand protection assay is an indication that the nucleotide analog/restriction endonuclease pair being tested will support SDA.

In all of the foregoing assays it was observed that the performance of dCTPαBH₃ was virtually identical to the performance of dCTPαS. As the site of modification on the boronated dNTP is the same as the site of modification on the thiolated dNTP, and the two groups are a similar size and have a similar charge, it can be concluded that most α-boronated dNTPs will mimic a corresponding α-thiolated dNTP in essentially all respects as regards SDA. It is therefore believed that the corresponding dNTPαBH₃ may be substituted for any of the dNTPαS known to induce nicking in any of the restriction endonuclease recognition sites previously identified for use with in SDA. That is, incorporation of the following alpha-boronated dNTPs into the indicated hemimodified restriction endonuclease recognition site should induce the nicking required for the SDA reaction as the corresponding dNTPαS does:

| RESTRICTION ENDONUCLEASE | RECOGNITION SITE (5'-3') | dNTP ANALOG |
|---|---|---|
| HincII | GTTGAC | dATPαBH₃ |
| HincII | GTCAAC | dGTPαBH₃ |
| AvaI | CCCGAG | TTPαBH₃ |
| AvaI | CTCGGG | dCTPαBH₃ |
| NciI | CCGGG | dCTPαBH₃ |
| HindII | GTTGAC | dATPαBH₃ |
| HindII | GTCAAC | dGTPαBH₃ |
| Fnu4HI | GCGGC | dCTPαBH₃ |
| BstXI | CCAAAACCCTGG (SEQ ID NO:1) | TTPαBH₃ |
| BstXI | CCAGGTTTTGG (SEQ ID NO:2) H₃ | dCTPαBH₃ |
| BsmI | AAAGCATTC | TTPαBH₃ |
| BsrI | AACCAGT | TTPαBH₃ |
| BsaI | GGTCTCTTTTTT (SEQ ID NO:3) | dATPαBH₃ |
| NlaIV | GGAACC | TTPαBH₃ |
| NspI | GCATGT | dCTPαBH₃ |
| NspI | GCATGT | dCTPαBH₃ & dGTPαBH₃ |
| PflMI | CCAGGTTTTGG (SEQ ID NO:4) | dCTPαBH₃ |
| HphI | GGTGAGGATCGTTT (SEQ ID NO:5) | dATPαH3 |
| AlwI | GGATCGTTTTT (SEQ ID NO:6) | dATPαBH₃ |
| FokI | GGATGGCATGTCTTTTGGG (SEQ ID NO:7) | dCTPαBH₃ |
| AccI | GTAGAC | dCTPαBH₃ |
| AccI | GTAGAC | TTPαBH₃ |
| AccI | GTAGAC | TTPαBH₃ & dCTPαBH₃ |
| AccI | GTCTAC | dATPαBH₃ |
| AccI | GTCTAC | dGTPαBH₃ |
| AccI | GTCTAC | dATPαBH₃ & dGTPαBH₃ |
| Tth111I | GACCACGTC | TTPαBH₃ |
| Tth111I | GACCACGTC | TTPαBH₃ & dGTPαBH₃ |
| Tth111I | GACGTGGTC | dCTPαBH₃ |
| Tth111II | GACGTGGTC | dCTPαBH₃ & dATPαBH₃ |
| MvaI | CCTGG | dATPαBH₃ |
| BalI | CCCGAGGAAGG (SEQ ID NO:8) | dCTPαBH₃ |
| BsmI | GAATGC | dCTPαBH₃ |
|  | GCATTC | dATPαBH₃ |
| BsmAI | GTCTC | dGTPαBH₃ & TTPαBH₃ |
|  | GTCTCCAATC (SEQ ID NO:9) | dGTPαBH₃ |
| BsoBI | CTCGGG | dCTPαBH₃ |
|  | CCCGAG | TTPαBH₃ |
| BsrI | CCAGT | dATPαBH₃ |
| BsrDI | CATTGC | TTPαBH₃ |
| BstNI | CCTGG | dATPαBH₃ & dCTPαBH₃ |
| BstOI | CCTGG | dATPαBH₃ & dCTPαBH₃ |
| BstXI | GGGTCTCCAGGAA (SEQ ID NO:10) | TTPαBH₃ |
| MwoI | GCAATGGCGGC (SEQ ID NO:11) | dGTPαBH₃ & TTPαBH₃ |

As the most commonly used modified dNTPs used in SDA are thiolated dNTPs, SDA has been optimized to produce highly efficient amplification using these reagents. While direct substitution of boronated dNTPs into SDA reactions optimized for thiolated dNTPs would not be expected to give optimum results, it is the most convenient method for demonstrating SDA in the presence of boronated dNTPs. dCTPαBH₃ was therefore tested in SDA reactions as generally performed with dNTPαS, using Bst (New England BioLabs) and Bca polymerases. The Bst reaction contained 25 mM K₂PO₄, pH 7.5; 0.1 μg/μl BSA; 0.05 μM each bumper primer; 0.5 μM each SDA amplification primer; 1.4 mM dCTPαS or dCTPαBH₃; 0.5 mM each dGTP, dUTP and dATP; 500 ng human DNA; 4×10⁵ targets (IS6110 insertion element of *Mycobacterium tuberculosis*); 10% glycerol; 120 units BsoBI and 60 units Bst. The reactions further included 6.9 mM, 7.6 mM or 8.4 mM MgCl₂, representing 4 mM, 4.7 mM or 5.5 mM free magnesium. The Bca reactions were similar, except for substitution of 35 mM K₂PO₄, pH 7.5; 0.2 mM each dGTP and dATP; 160 units BsoBI, 8 units Bca. The Bca reactions included 5.5 mM, 6 mM or 6.5 mM MgCl₂, representing 3.2 mM, 3.7 mM and 4.2 mM free magnesium. All SDA reactions were prepared containing all reagents except enzymes and MgCl₂, then denatured at 100° C. for 3 min. The reactions were then cooled to 55° C. for 2 min. and the polymerase, restriction endonuclease and MgCl₂ were added and mixed. Amplification was allowed to proceed at 55° C.

for 30 min. The reactions were terminated by quickly freezing the samples on dry ice.

Amplification was detected by electrophoresis over 10% non-denaturing gels and staining with ethidium bromide. Alternatively, a radioactively end-labeled detector probe was hybridized to the amplification products and extended as follows: 5 μl of 1 μM detector probe in 35 mM $K_2PO_4$, 1 mM each dNTP, 4–6 mM $MgCl_2$ was added to the amplification reaction and the mixture was denatured for 2 min. at 100° C. The samples were equilibrated at 37° C. for 1 min. and 1 unit of exo⁻ Klenow polymerase was added. The extension reaction was incubated at 37° C. for 10 min., stopped by addition of 11 μl of formamide and electrophoresed over an 8% sequencing gel. The extended detector probe was visualized by autoradiography.

The target was successfully amplified in the presence of dCTPαBH$_3$, with amplification factors of about $10^4$ to $3 \times 10^5$. These amplification factors were about 1000-fold less than those obtained in the dCTPαS reaction, however, as discussed above, a reduction in amplification efficiency is not unexpected as the reactions were not optimized for incorporation of boronated dNTPs. This experiment clearly demonstrates that incorporation of dNTPαBH$_3$ in SDA supports target amplification.

What is claimed is:

1. A method for amplifying a target nucleic acid sequence by SDA comprising amplifying the target nucleic acid sequence in an SDA reaction wherein an alpha-boronated deoxynucleoside triphosphate is incorporated into a double-stranded recognition site for a restriction endonuclease, thereby producing a hemimodified restriction endonuclease recognition site which is nicked by the restriction endonuclease during the SDA reaction.

2. The method of claim 1 wherein the alpha-boronated deoxynucleoside triphosphate is 2'-deoxycytidine-α-borano-triphosphate.

3. The method of claim 2 wherein the restriction endonuclease is BsoBI.

4. The method of claim 2 wherein the recognition site is CTCGGG.

5. The method of claim 1 wherein the restriction endonuclease is selected from the group consisting of HincII, AvaI, Fnu4HI, NciI and BsrI.

6. A method for producing nickable double-stranded DNA comprising incorporating an alpha-boronated deoxynucleoside triphosphate into a double-stranded recognition site for a restriction endonuclease to produce a hemimodified recognition site, thereby rendering the recognition site nickable by the restriction endonuclease.

7. The method of claim 6 wherein the boronated deoxynucleoside triphosphate is 2'-deoxycytidine-α-borano-triphosphate.

8. The method of claim 7 wherein the restriction endonuclease is BsoBI.

9. The method of claim 8 wherein one strand of the double-stranded recognition site is CTCGGG.

10. The method of claim 6 wherein the restriction endonuclease is selected from the group consisting of HincII, AvaI, Fnu4HI, NciI and BsrI.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

CCAAAACCCT GG     12

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

CCAGGTTTTG G     11

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

GGTCTCTTTT TT     12

( 2 ) INFORMATION FOR SEQ ID NO:4:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

CCAGGTTTTG G     11

( 2 ) INFORMATION FOR SEQ ID NO:5:

( i ) SEQUENCE CHARACTERISTICS:
        ( A ) LENGTH: 14 base pairs ( B ) TYPE: nucleic acid
( C ) STRANDEDNESS: double
( D ) TOPOLOGY: linear ( x i ) SEQUENCE DESCRIPTION: SEQ ID NO:5:

GGTGAGGATC GTTT  14

( 2 ) INFORMATION FOR SEQ ID NO:6:

( i ) SEQUENCE CHARACTERISTICS:
( A ) LENGTH: 11 base pairs
( B ) TYPE: nucleic acid
( C ) STRANDEDNESS: double
( D ) TOPOLOGY: linear ( x i ) SEQUENCE DESCRIPTION: SEQ ID NO:6:

GGATCGTTTT T  11

( 2 ) INFORMATION FOR SEQ ID NO:7:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( x i ) SEQUENCE DESCRIPTION: SEQ ID NO:7:

GGATGGCATG TCTTTTGGG  19

( 2 ) INFORMATION FOR SEQ ID NO:8:

( i ) SEQUENCE CHARACTERISTICS:
( A ) LENGTH: 11 base pairs
( B ) TYPE: nucleic acid
( C ) STRANDEDNESS: double
( D ) TOPOLOGY: linear ( x i ) SEQUENCE DESCRIPTION: SEQ ID NO:8:

CCCGAGGAAG G  11

( 2 ) INFORMATION FOR SEQ ID NO:9:

( i ) SEQUENCE CHARACTERISTICS:
( A ) LENGTH: 10 base pairs
( B ) TYPE: nucleic acid
( C ) STRANDEDNESS: double
( D ) TOPOLOGY: linear ( x i ) SEQUENCE DESCRIPTION: SEQ ID NO:9:

GTCTCCAATC  10

( 2 ) INFORMATION FOR SEQ ID NO:10:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( x i ) SEQUENCE DESCRIPTION: SEQ ID NO:10:

GGGTCTCCAG GAA  13

( 2 ) INFORMATION FOR SEQ ID NO:11:

( i ) SEQUENCE CHARACTERISTICS:
( A ) LENGTH: 11 base pairs
( B ) TYPE: nucleic acid
( C ) STRANDEDNESS: double ( D ) TOPOLOGY: linear ( x i ) SEQUENCE DESCRIPTION: SEQ ID NO:11:

GCAATGGCGG C                                                                                                  11